United States Patent [19]
Dent

[11] Patent Number: 5,609,060
[45] Date of Patent: Mar. 11, 1997

[54] MULTIPLE CHANNEL PERFUSED MANOMETRY APPARATUS AND A METHOD OF OPERATION OF SUCH A DEVICE

[75] Inventor: John Dent, Belair, Australia

[73] Assignee: Dentsleeve Pty Limited, Australia

[21] Appl. No.: 431,052

[22] Filed: Apr. 28, 1995

[51] Int. Cl.$^6$ .................................................. G01L 13/04
[52] U.S. Cl. .................................................. 73/700; 73/747
[58] Field of Search ........................................ 73/700, 747

[56] References Cited

PUBLICATIONS

Improved Infusion System for Intraluminal Esophageal Manometry, by Ronald C. Arndorfer, John J. Stef, M.S.M.E., Wylie, J. Dodds, M.D., John H. Linehan, Ph.D., M. E., and Walter J. Hogan, M.D., published in Gastroenterology 73:23–27, 1977.

Intraluminal Esophageal Manometry: An Analysis of Variables Affecting Recording Fidelity of Peristaltic Pressures, by John J. Stef, Wylie J. Dodds, M.D., Walter J. Hogan, M.D., John H. Linehan, Ph.D., M.E., and Edward T. Stewart, M.D., published in Gastroenterology 67:221–230, 1974.

A. Pneumatically Driven Pump for Constant Perfusion Manometry, by J. Dent, J. Culross and J. M. Morris, published in The Australian Journal of Experimental Biology and Medical Science, vol. 55 (1977).

Instrumentation and Methods for Intraluminal Esophageal Manometry, by Wylie J. Dodds, M.D., published in Arch Intern Med–vol. 136, May 1976.

Rubber Extrusions at Low Perfusion Rates, by T. Omari, J. Dent, M. Bakewell, R. Fraser, and G. Davidson, published in Gastroenterology 107:1297, Oct. 1994.

*Primary Examiner*—V. Millin
*Assistant Examiner*—Robert N. Wieland
*Attorney, Agent, or Firm*—Evenson, McKeown, Edwards & Lenahan P.L.L.C.

[57] ABSTRACT

An apparatus for multiple channel perfused gastrointestinal manometry particularly useful for animals and small children which avoids errors in pressure measurement due to air bubbles, particularly micro- bubbles in the channels. Achieved by the use of a carbon dioxide flush of the apparatus to displace the air bubbles in the manifold and manometry lines. The carbon dioxide is subsequently dissolved in the subsequent flow of manometric infusate.

20 Claims, 3 Drawing Sheets

5,609,060

MULTIPLE CHANNEL PERFUSED MANOMETRY APPARATUS AND A METHOD OF OPERATION OF SUCH A DEVICE

TECHNICAL FIELD

This invention relates to a multiple channel perfused manometry apparatus and a method of operation of such a device for medical purposes particularly for gastrointestinal manometry.

DISCUSSION OF PRIOR ART

Conventionally perfused gastrointestinal manometry uses a bundle of individual channels that are formed into a manometric line assembly. Each channel opens at a specific level or distance along the manometric assembly and enables the monitoring of the pressure occurring at that particular point. Simultaneous recording from multiple channels is informative about mechanical functioning of the region of the gastrointestinal tract being studied as the patterning of movement of pressure waves caused by the contractions of that segment of the gut can be analysed with confidence on the basis of the pressures recording.

The standard sensor that is used with perfused luminal manometry consists of a single channel which opens to the lumen of the gut through a side hole cut in its wall. The lumen of the channel is plugged just below the side hole opening.

Pressures are recorded with an array of pressure transducers external to the body. Each channel connects to its own pressure transducer which converts the pressures transmitted to it up the manometric assembly into electrical signals that are then processed, displayed and stored on a recording device.

There are significant challenges with faithful transmission of pressures occurring within the gut lumen at the side hole opening up to the pressure transducer itself.

A first problem is supplying manometric infusate at a sufficiently steady pressure and flow rate so that accuracy is obtained.

It is well established that mere filling of the manometric assembly channels with water is insufficient to ensure effective transmission of luminal pressures to the transducer. It is known that if water is infused down manometric channels this greatly improves the fidelity of pressure transmission to the external transducer. The infusion tensions the manometric channel against the increased resistance to pressure outflow caused by a pressure transient in the lumen which causes expansion of the volume of the channel between the side opening and the transducer. Unless the increased volume of the hydraulic link between the transducer and the point of luminal measurement is filled by addition of volume to the system when contraction occurs at the side hole recording point, the lining of the gut plugs the side hole with the retreat of water back up the assembly. In these circumstances the pressure recorded does not reflect accurately the squeeze of the contraction on the recording point. Constant infusion of water into the channel can allow for the expansion of the channel and so counteract the squeeze of the gut contraction, maintaining outflow of water from the side hole in the channel and thus ensuring complete tensioning of the fluid link between the gut lumen and the transducer. Provided outflow is maintained from the side hole during contraction of the gut around it then the pressure that is transmitted up the manometric line assembly to the transducer is a faithful reflection of the pressure occurring within the lumen.

A piece of equipment which is vital in ensuring effective transmission of luminal pressures to the transducer is a low compliance manometric infusion pump. Such a device is explained in the article "A pneumatically driven pump for constant perfusion manometry" by Dent, Culross and Morris (Australian Journal of Experimental Biology and Medicine Science, Volume 55, 1977, pages 293–298).

As can be seen the points discussed above indicate the importance of minimisation of the stretchiness or compliance of the manometric channel between the point of occurrence of contraction and the transducer. The greater the compliance the higher the rate of infusion must be to overcome it. Compliance of a manometric line assembly can be considered as being in two major categories, inevitable compliance which is due to the physical properties of the material from which the manometric line assembly is made and avoidable compliance which results from two main factors. Avoidable compliance may be caused by bubbles trapped within the manometric lines or inadequate sealing of connections which allow shearing of contact surfaces on the conditions of increased manometric line assembly pressure.

It will be noted that inevitable compliance can be greatly minimised by good manometric assembly design but it is the object of this invention to provide an arrangement and method to minimise avoidable compliance.

The use of a flow of manometric infusate with a standard low compliance manometric infusion pump does not automatically enable removal of bubbles from the manometric line assembly and these bubbles are by far the most important source of avoidable compliance. The user of such equipment needs to pay close attention to vibration of connectors to dislodge bubbles trapped at joints and irregularities in manometric channels. Forcible flushing of channels with syringes at the stage of set up is partially successful in removing bubbles but even so all bubbles cannot be removed and particularly as manometric channels become smaller, then the adherence of bubbles to the internal surface of manometric channels due to surface tension is of concern.

These problems are particularly of concern where micro manometry is used where instead of manometric channels having 0.65 to 0.75 mm diameter, sizes may go down to as low as 0.28 mm. The miniaturisation of manometric assemblies to such dimensions can effectively render conventionally designed manometric assemblies obsolete. The miniaturisation extends very substantially the settings in which gastrointestinal manometry can be done. This is especially important in measurements in babies and animals.

It is to overcome the problem of accuracy of such assemblies that the present invention is directed.

SUMMARY OF THE INVENTION

In one form therefore the invention is said to reside in a perfused manometry apparatus comprising a manometric line assembly having a plurality of channels therein with each channel terminating towards an operative end of the manometric line assembly at an opening in the line at a selected distance along the line, a manifold including a plurality of outlets for supplying a manometric infusate under pressure to each of the channels via the outlets at a manifold end of the manometric line assembly and the transducer associated with each channel to measure the pressure in each of the channels, the manifold including a flushing gas inlet to allow for introduction of a flushing gas into the manifold and an infusate inlet to allow for introduction of the manometric infusate into the manifold, the first inlet means being connected with a source of flushing gas and the second inlet means being in connection with a source of manometric infusate under pressure.

In an alternate form the invention is said to reside in a method of flushing a perfused manometry apparatus to remove air bubbles before introduction of a manometric infusate, the perfused manometry apparatus comprising a manometric line assembly having a plurality of channels therein with each channel terminating towards an operative end of the manometric line assembly at an opening in the line at a selected distance along the line, a manifold including a plurality of outlets for supplying a manometric infusate under pressure to each of the channels via the outlets at a manifold end of the manometric line assembly and the transducer associated with each channel to measure the pressure in each of the channels, the manifold including a flushing gas inlet to allow for introduction of a flushing gas into the manifold and a infusate inlet to allow for introduction of the manometric infusate into the manifold, the first inlet means being connected with a source of flushing gas and the second inlet means being in connection with a source of manometric infusate under pressure, the method comprising the steps of allowing a flow of the flushing gas through the first inlet into the manifold and subsequently into the transducers and into the channels of the manometric line assembly to exit out of the openings, stopping the flow of the flushing gas, and allowing a flow of manometric infusate into the manifold to replace the flushing gas throughout the apparatus, whereby any remaining flushing gas is dissolved in the manometric infusate and carried out of the opening by the flow of infusate.

It will be realised that by having a flushing gas which is readily soluble in the manometric infusate and which replaces air in the manifold and channels then air bubbles are removed.

The manometric infusate may be de-gassed distilled water and the flushing gas may be carbon dioxide.

The very narrow channels in miniaturised extrusions for manometry have a very much higher resistance to the flow of infusate through them. Consequently the use of a standard infusion rate of 0.6 ml/min per channel produces an unacceptably high pressure gradient along the manometric channel. Furthermore in the settings in which such miniature manometric assemblies would be used the rates of fluid delivery associated with making measurements would be entirely unacceptable. The use of carbon dioxide flushing along with miniaturised manometric assembly has enabled much lower flow rates of manometric infusion down to as low as 0.01 ml/min. Thus a comparable recording fidelity is achieved with a micro manometric assembly at an infusion rate one sixtieth of that which was being used conventionally.

This then generally describes the invention but to assist with understanding reference will now be made to the. accompanying drawings showing preferred embodiments of the invention and specific examples.

DETAILED DESCRIPTION OF THE DRAWINGS

Figure 1:
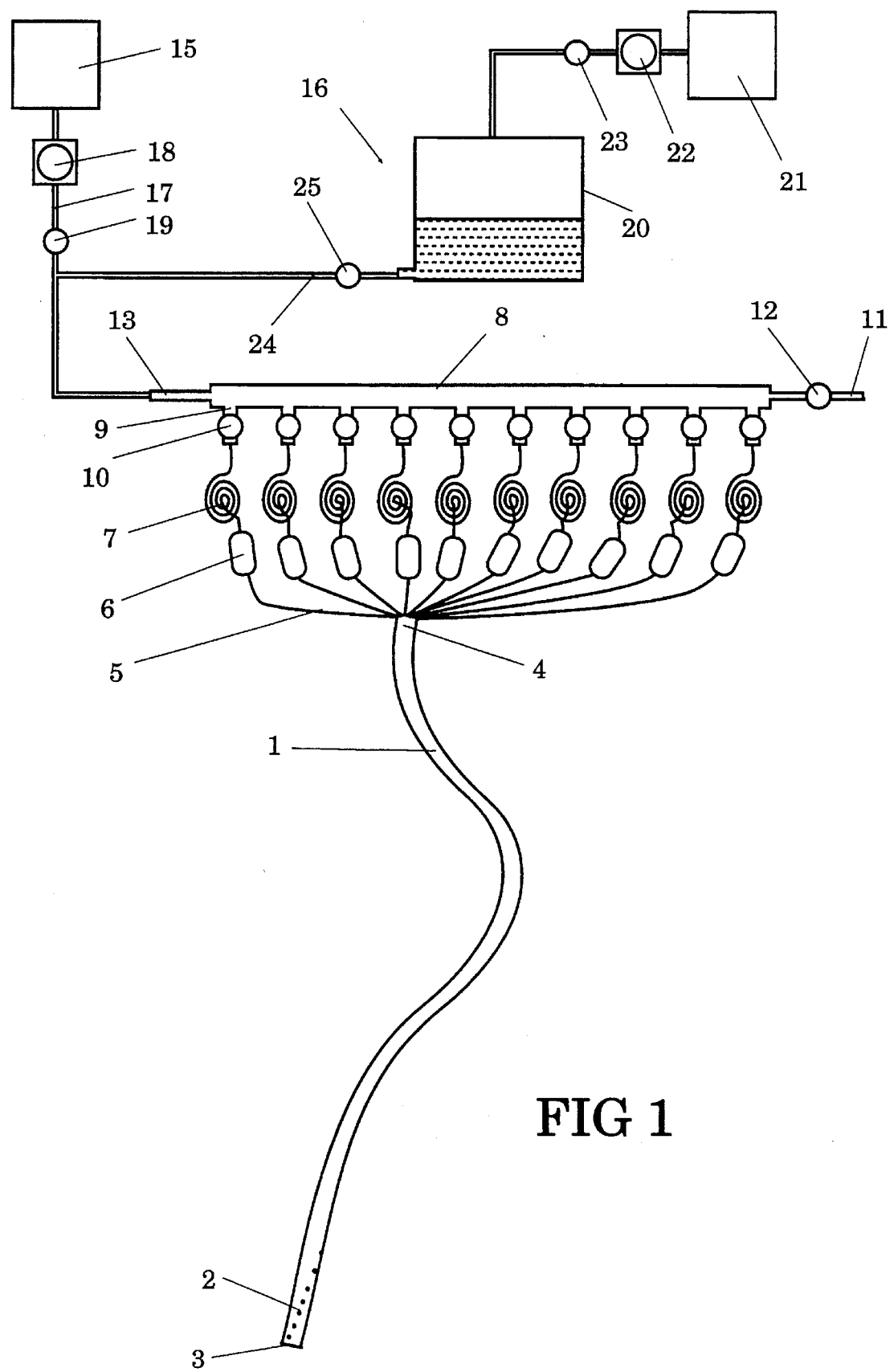
FIG. 1 shows a stylised view of a multiple channel perfused manometry apparatus according to this invention.

FIG. 1 shows a stylised view of a multiple channel perfused manometry apparatus according to this invention. The apparatus includes a manometric line assembly 1 which includes a number of openings 2 at an operative end 3 of the manometric line assembly. The manometric line assembly 1 comprises a plurality of channels with each channel connected at the manifold end 4 of the manometry line 1 by means of a flow line 5 through a transducer 6 and hydraulic resistance 7 to a manifold 8. The manifold 8 has a plurality of outlets 9 and each outlet has a valve 10.

The manifold 8 also includes a purge outlet 11 and a purge valve 12. A common inlet 13 is provided into the manifold 8 from a source of carbon dioxide 15 and a pneumatically driven perfusion pump generally shown as 16. The line 17 from the carbon dioxide source 15 includes a pressure regulator 18. The line 17 from the carbon dioxide source 15 also includes a valve 19.

The pneumatically driven perfusion pump 16 comprises a water reservoir 20 which is supplied by air from an air source 21 via an air pressure regulator 22 and an air valve 23 and water is forced out of the reservoir 20 through line 24 when valve 25 is opened. Hence the device 16 acts as a pump.

Figure 3:
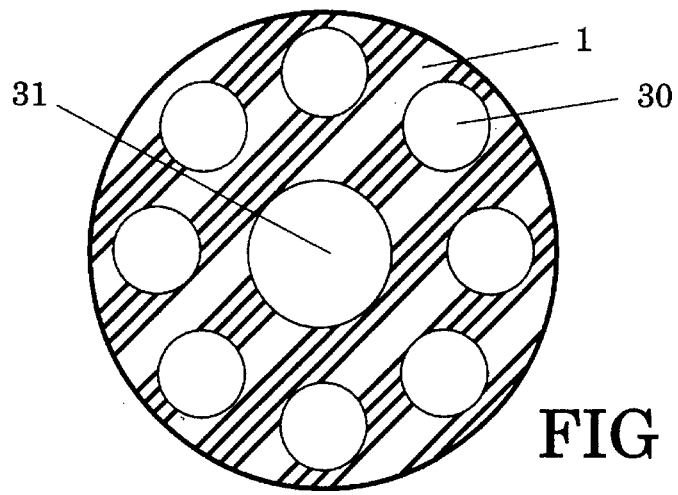
FIG. 3 shows a cross sectional view of a manometric line assembly according to this invention.
Figure 4:
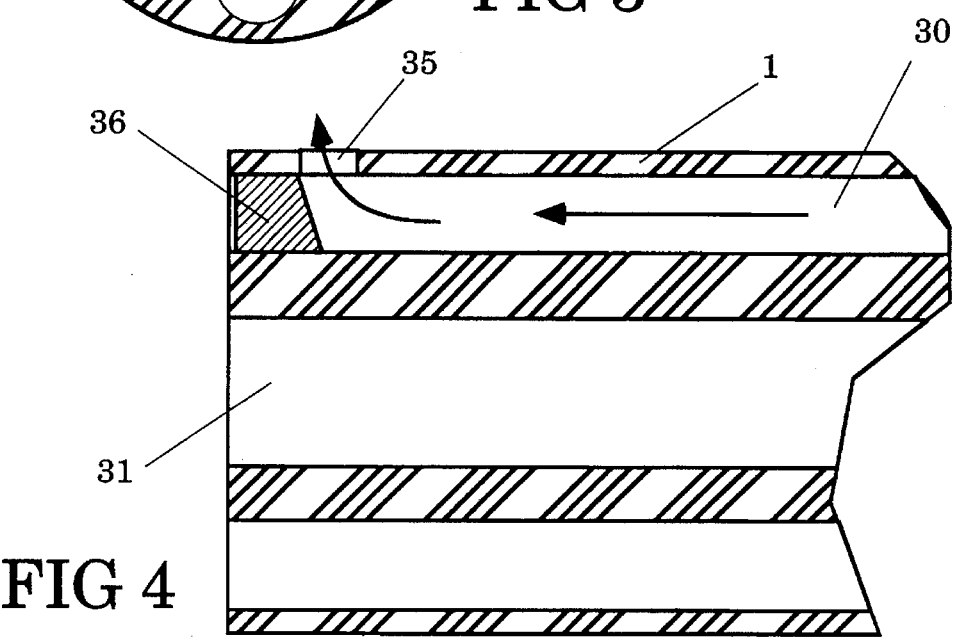
FIG. 4 shows the method of making an opening in a manometric line assembly according to this invention.
Figure 5:
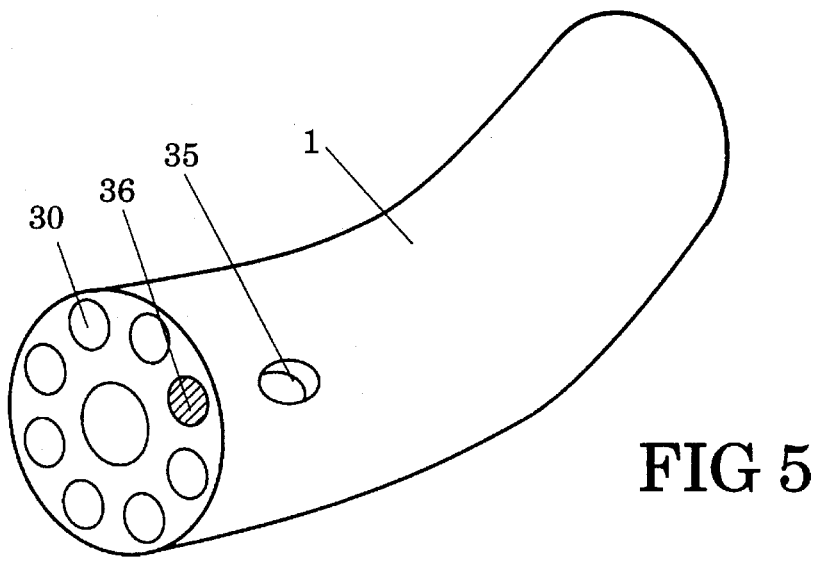
FIG. 5 shows a perspective view of a portion of manometric line assembly according to this invention.

The perfused manometry line shown in FIGS. 3, 4 and 5 comprises an extruded, preferably silicon rubber, casing having eight but possibly ranging from four to twenty one channels 30 around the periphery and usually one larger channel 31 which may be in the middle of the extrusion although it may be eccentrically positioned. At selected points along the length of the manometric line assembly 1 openings 35 are made into the extrusion so that they each open into one of the channels 30. A plug 36 is placed into each of the channels 30 downstream from its respective opening 35. During operation of the manometry apparatus a constant flow of manometric infusate such as degassed distilled water is allowed to flow out through the openings 35 and changes in pressure outside the openings 35 are reflected back along the channel 30 to the transducers 6 as seen in FIG. 1 and this gives an indication of the pressure around the opening.

The openings 35 from the channels 30 through the wall of the manometry line 1 may be placed at any required spacing depending upon the length of measurement of the gut required. In preferred embodiments spacings may be in the range of 1 mm apart along the length of the manometric line assembly 1 up to 5 cm apart.

Now looking at FIG. 2 the four stages in flushing of the multiple channel perfused manometry apparatus to remove any air bubbles which may be trapped in the various channels and tubes are shown. In FIG. 2A, B, C and D the use of a thick line indicates a flow in that line and a thin line indicates no flow in that line.

Figure 2A:
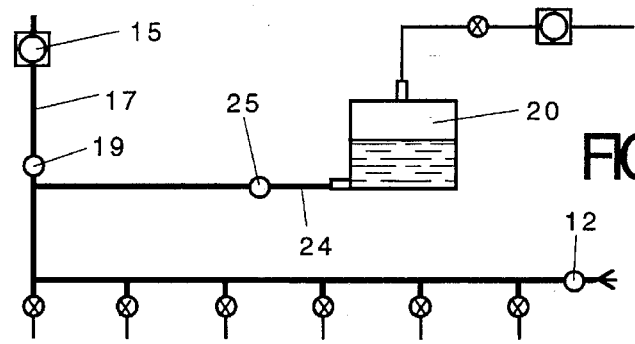
FIGS. 2A–2D shows four stages of the flushing of air bubbles out of the apparatus according to FIG. 1.

In FIG. 2A valve 19 in line 17 has been opened and valve 25 in line 24 has also been opened and carbon dioxide is allowed to flow through the pressure regulator 15 into the reservoir 20. At the same time valve 12 is opened and carbon dioxide can flow through the manifold and out of the purge outlet. By this means any trapped manometric infusate in the manifold will be taken out of the system. Valve 25 is only opened so that any air in the line 24 is displaced into the reservoir 20.

Figure 2B:
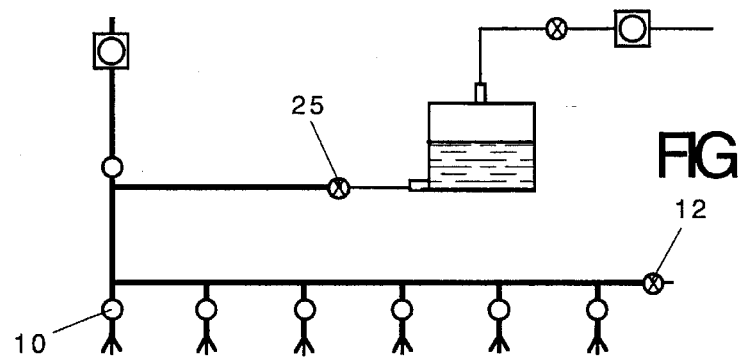
Figure 2C:
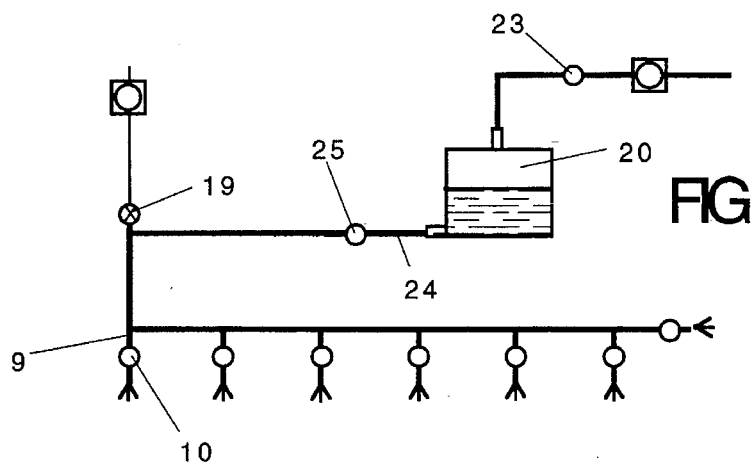

In a second stage shown in FIG. 2B the valves 25 and 12 are closed and the valves 10 on the manifold outlets are opened so that carbon dioxide can flow from the manifold through each of the outlets and subsequently to the channels 30 of the manometry line 1 to exit out of the openings 35 (not shown in FIG. 2).

After the carbon dioxide has been allowed to flow for a sufficient time the carbon dioxide control valve 19 is closed and the air supply valve 23 is opened and the valve 25 in the line 24 is also opened. The purge outlet valve in the manifold 12 is opened and the pump 16 operates so that manometric infusate from the reservoir 20 can flow through the line 24 and into the manifold inlet 13. Manometric infusate flows out of the purge outlet 11 as well as through each of the outlets 9 through the outlet valves 10 and subsequently into the manometric line assembly 1 to flow out of the openings 35 in the manometric line assembly and to take with them any dissolved carbon dioxide.

Figure 2D:
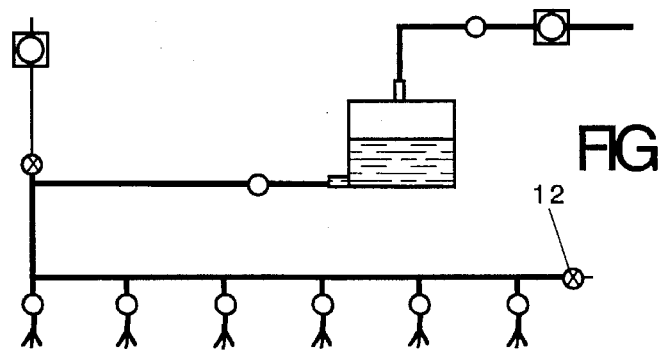

Subsequently as shown in FIG. 2D the purge outlet valve 12 is closed so that manometric infusate will only flow out of the manifold outlets into the manometry line.

Preferably the flow of manometric infusate is allowed for up to five minutes before the multiple channel perfused manometry apparatus is ready for use.

It will be realised that the stages of flushing discussed above may be done manually or the entire cycle may be done automatically. There may be provided microprocessor control of the carbon dioxide flush procedure with automated cycling of valve openings and closings.

There may also be provided alarm systems, possibly both visible and audible, when sensors indicate abnormal operating conditions. Major abnormal conditions may include an under or over pressure of the compressed gas supply for driving infusate and the carbon dioxide flush.

The manometric infusate for gastrointestinal measurements may be degassed distilled water or brine and may be filtered to remove particles which may otherwise block up the hydraulic resistances and the channels in the manometric line assembly.

The manometric line assemblies suitable for this invention may have diameters from 3 mm to 5 mm with channels within the line having diameters in the range of 0.6 to 0.8 mm.

Miniature and micro manometric line assembly extrusions may have diameters in the range of 1.75 to 4 mm and have manometric channels in the range of diameters from 0.28 mm up to 0.6 mm.

There may be from four channels up to twenty one channels in each manometric line assembly.

The material of construction of the miniature and micromanometric line assembly extrusions may be selected from silicone rubber, urethane rubbers, thermoplastics, thermorubbers or any other suitable material.

The pressure of the air driving the pneumatically operated pump may be up to 100 kilopascals.

The hydraulic resistance may be made from capillary tubing and the internal diameter or the overall length of the capillary tubes may be selected to provide flow rate in the range of 0.01 ml/min to 0.6 ml/min.

The claims defining the invention are as follows:

1. A perfused manometry apparatus comprising a manometric line assembly having a plurality of channels therein with each channel terminating towards an operative end of the manometric line assembly at an opening in the line at a selected distance along the line, a manifold including a plurality of outlets for supplying a manometric infusate under pressure to each of the channels via the outlets at a manifold end of the manometric line assembly and the transducer associated with each channel to measure the pressure in each of the channels, the manifold including a flushing gas inlet to allow for to introduction of a flushing gas into the manifold and a infusate inlet to allow for introduction of the manometric infusate into the manifold, the first inlet means being connected with a source of flushing gas and the second inlet means being in connection with a source of manometric infusate under pressure.

2. A perfused manometry apparatus as in claim 1 further including a hydraulic resistance in each manifold outlet whereby to restrict the flow of manometric infusate into the channels.

3. A perfused manometry apparatus as in claim 2 wherein the hydraulic resistance comprises a capillary tube of a selected length to provide a selected resistance to flow.

4. A perfused manometry apparatus as in claim 1 wherein the manifold further includes a purge outlet.

5. A perfused manometry apparatus as in claim 4 wherein the flushing gas inlet and the infusate inlet are at one end of the manifold and the purge outlet is at the other end of the manifold.

6. A perfused manometry apparatus as in claim 1 wherein each manifold outlet includes a valve.

7. A perfused manometry apparatus as in claim 1 wherein the manometric infusate is de-gassed distilled water.

8. A perfused manometry apparatus as in claim 1 wherein the flushing gas is carbon dioxide.

9. A perfused manometry apparatus as in claim 1 in which the manometric line assembly is a micro-extrusion.

10. A perfused manometry apparatus as in claim 1 wherein the manometric line assembly has from four to twenty one channels.

11. A perfused manometry apparatus as in claim 1 wherein the manometric line assembly is a silicone rubber extrusion having the channels moulded therein.

12. A perfused manometry apparatus as in claim 1 wherein the channels have a diameter of from 0.20 mm to 0.80 mm.

13. A perfused manometry apparatus as in claim 1 wherein the source of manometric infusate under pressure is a pneumatically driven perfusion pump and a pneumatic source for the pump includes a pressure regulator.

14. A perfused manometry apparatus as in claim 1 wherein the source of carbon dioxide includes a pressure regulator.

15. A method of flushing a perfused manometry apparatus to remove air bubbles before introduction of a manometric infusate, the perfused manometry apparatus comprising a manometric line assembly having a plurality of channels therein with each channel terminating towards an operative end of the manometric line assembly at an opening in the line at a selected distance along the line, a manifold including a plurality of outlets for supplying a manometric infusate under pressure to each of the channels via the outlets at a manifold end of the manometric line assembly and the transducer associated with each channel to measure the pressure in each of the channels, the manifold including a flushing gas inlet to allow for introduction of a flushing gas into the manifold and a infusate inlet to allow for introduction of the manometric infusate into the manifold, the first inlet means being connected with a source of flushing gas and the second inlet means being in connection with a source of manometric infusate under pressure, the method comprising the steps of allowing a flow of the flushing gas through the first inlet into the manifold and subsequently into the transducers and into the channels of the manometric line assembly to exit out of the openings, stopping the flow of the flushing gas, and allowing a flow of manometric infusate into the manifold to replace the flushing gas throughout the apparatus, whereby any remaining the flushing gas is dissolved in the manometric infusate and carried out of the opening by the flow of infusate.

16. A method as in claim 15 wherein the carbon dioxide is allowed to flow for approximately two minutes.

17. A method as in claim 15 wherein the flow of manometric infusate subsequent to the flow of carbon dioxide is allowed for at least five minutes before the apparatus is used.

18. A method as in claim 15 wherein the manifold further includes a purge outlet and a purge outlet valve and the method includes the step of first opening the purge outlet valve and purging any liquid from the manifold by a flow of carbon dioxide.

19. A method as in claim 15 wherein the flushing gas is carbon dioxide.

20. A method as in claim 15 wherein the manometric infusate is degassed distilled water.

* * * * *